United States Patent [19]
Gendron et al.

[11] Patent Number: 5,918,473
[45] Date of Patent: Jul. 6, 1999

[54] METHOD AND APPARATUS FOR MEASURING QUENCHANT PROPERTIES OF COOLANTS

[75] Inventors: André Gendron; Thierry Bourgeois, both of Jonquière; Yves Caron, Chicoutimi, all of Canada

[73] Assignee: Alcan International Limited, Montreal, Canada

[21] Appl. No.: 08/854,104

[22] Filed: May 9, 1997

[51] Int. Cl.[6] .................................................. G01N 25/00
[52] U.S. Cl. ................................ 62/129; 374/43; 164/455
[58] Field of Search ............................. 62/129, 130, 201, 62/185, 126, 127; 165/287, 299, 300, 295; 374/43, 44, 45, 39, 40, 41, 54; 164/455

[56] References Cited

U.S. PATENT DOCUMENTS

| | | | |
|---|---|---|---|
| 2,717,515 | 9/1955 | Pesante | 374/43 |
| 2,937,334 | 5/1960 | Bolston et al. | |
| 3,142,170 | 7/1964 | Calhoun | 374/43 X |
| 4,106,331 | 8/1978 | Bunton et al. | 73/61.1 R |
| 4,412,752 | 11/1983 | Cellitti et al. | 374/43 |
| 4,563,097 | 1/1986 | Katafuchi | 374/43 |
| 4,636,089 | 1/1987 | Schumann | 374/45 |
| 4,722,611 | 2/1988 | Hultgren | 374/43 |
| 4,756,357 | 7/1988 | Bänninger et al. | 164/455 |
| 4,987,950 | 1/1991 | Yu | 164/455 |
| 5,148,853 | 9/1992 | Yu et al. | 164/455 |
| 5,178,463 | 1/1993 | Berry, Jr. et al. | 374/43 |
| 5,289,867 | 3/1994 | Barker et al. | 164/455 |
| 5,601,363 | 2/1997 | Keil et al. | 374/45 |

FOREIGN PATENT DOCUMENTS

| | | |
|---|---|---|
| 36 23 158 A1 | 1/1988 | Germany. |
| 60-190847 | 9/1985 | Japan. |

OTHER PUBLICATIONS

"A Sensor for Monitoring the Heat Transfer Characteristics of Ingot Cooling Water Containing Dissolved Gases", H. Yu et al., Light Metals 1994, The Metallurgical Society of the AIME, pp. 779–786.

"The Effect of Cooling Water Quality on Aluminum Ingot Casting", H. Yu, Light Metals 1985, The Metallurgical Society of the AIME, pp. 1331–1347.

"Measuring the Heat Extraction Capacity of DC Casting Cooling Water", Langlais et al., Light Metals 1995, The Metallurgical Society of the AIME, pp. 979–986.

"Process Simulation of High Heat Flux Casting Cooling Systems", Smyrniotis et al., Light Metals 1989, The Metallurgical Society of the AIME, pp. 881–891.

*Primary Examiner*—Harry B. Tanner
*Attorney, Agent, or Firm*—Cooper & Dunham LLP

[57] ABSTRACT

A method of measuring the quenchability of a liquid coolant used to cool objects such as ingots produced by direct-chill casting. The method involves providing a sample of the liquid coolant; providing a probe for immersion in the sample, the probe having a temperature-sensing electrical device contained therein which generates an electrical response corresponding to temperature sensed; heating the probe in a gas, preferably by means of electrical resistance heating by a circuit which is electrically connected to the temperature-sensing electrical device, to a predetermined temperature measured by the electrical response of the temperature sensing device, immersing the probe into the sample and measuring the electrical response for a predetermined measurement period, and comparing the measured electrical response to a response of a reference liquid measured under equivalent conditions, to thereby determine the quenchability property of the liquid coolant. The invention also relates to apparatus for carrying out the method, as well as a method and apparatus for controlling the cooling of the object based on the measured quenchability of the coolant. In an alternative, the probe may be heated by means other than the electrical resistance heating at a rate of at least about 40° C./second.

35 Claims, 5 Drawing Sheets

METHOD AND APPARATUS FOR MEASURING QUENCHANT PROPERTIES OF COOLANTS

BACKGROUND OF THE INVENTION

I. Field of the Invention

This invention relates to a method and apparatus for the measurement of the quenchant properties of coolants, and in particular the use of such methods and apparatus for measurement of properties of coolants used in the direct chill (DC) casting of metals, particularly aluminum alloys. It also relates to the use of such a method and apparatus for control of coolants in casting processes.

II. Discussion of the Background Art

It is recognized that the quenching properties of coolants, particularly those used in cooling aluminum alloy slabs from high temperatures during casting, are very dependent on the coolant composition, including the presence of small amounts of contaminants. This is particularly important when such coolants are to be used above the "film boiling temperature," since the effectiveness of cooling can be rapidly altered by slight changes to the film boiling temperature itself.

Various techniques have been used to measure the quenchant properties of coolants in the past. For example, U.S. Pat. No. 5,178,463 (Berry et al) describes the use of a flame-heated plate on which the quenchant to be tested is sprayed, and the temperature gradient is used to determine quenchant properties.

U.S. Pat. No. 4,756,357 (Banniger et al) describes an electrically-heated plate within a casting mould where the flowing coolant passes the plate and the heat loss is measured. The signal is subsequently used for controlling the coolant flow or gas content.

Both these methods employ fairly large heated elements and require the use of substantial quantities of flowing coolant.

A paper entitled "The Effect of Cooling Water on Aluminum Ingot Casting" by H. Yu, describes a small cylindrical element containing a thermocouple which is preheated in a furnace then immersed in a sample of coolant. While this device is more compact than the devices required for the preceding methods, a separate preheating furnace is required, and the thermal response is limited because of the slow response time of the embedded thermocouple.

There is a need, therefore, for a compact and fast response system for measuring coolant quenchant properties, including properties above the film boiling temperature, that can also serve as part of a control system for altering the coolant flow or properties in response to changes in such quenchant properties.

SUMMARY OF THE INVENTION

It is an object of the invention to provide a method for measuring the quenchant properties of coolants that is compact, rapid and precise.

Another object of the invention is to provide an apparatus for measuring the quenchant properties of coolants that is rapid and precise.

It is a further object of the invention to provide a method and apparatus for controlling the cooling of an object by intermittent but rapid measurement of the quenchant properties of the coolant and consequent alteration of the coolant flow or properties.

According to one aspect of the invention, there is provided a method of measuring quenchability of a liquid coolant, comprising the steps of: obtaining a sample of said liquid coolant; providing a probe for immersion in said sample, said probe comprising a temperature-sensing electrical device which generates an electrical response corresponding to temperature sensed; by means of electrical resistance heating by a circuit which is electrically connected to said temperature-sensing electrical device, heating said probe in a gas to a predetermined temperature measured by the electrical response of said temperature sensing device; immersing the said probe into said sample and measuring the electrical response for a predetermined measurement period, and comparing the measured electrical response to a response of a reference liquid measured under equivalent conditions; and determining quenchability of the liquid coolant from said responses.

According to another aspect of the invention, there is provided a method of measuring the quenchability of a liquid coolant, involving obtaining a sample of the liquid coolant, providing a probe for immersion in the sample, the probe comprising a temperature-sensing electrical device which generates an electrical response corresponding to a temperature sensed, heating the probe in a gas, at an average rate that exceeds 40° C./second, to a predetermined temperature measured by the electrical response of the temperature sensing device, immersing the probe into the sample and measuring the electrical response for a predetermined measurement period, and comparing the measured electrical response to a response of a reference liquid measured under equivalent conditions, to thereby determine the quenchability property of the liquid coolant.

According to another aspect of the invention, there is provided an apparatus for measuring quenchability of a liquid coolant, comprising: a probe for immersion in a sample of said liquid coolant; a temperature sensing electrical device contained within said probe; and an electrical resistance heating device contained within the probe.

According to another aspect of the invention, there is provided a method of controlling the cooling of an object by contacting the said object with a coolant, comprising the steps of: obtaining a substantially stagnant sample of said coolant; measuring quenchability of said coolant of said sample; and controlling a property of said coolant coming into contact with said object responsive to a measured quenchability of said coolant of said stagnant sample to achieve a desired cooling effect; wherein said quenchability is measured by providing a probe for immersion in said liquid coolant, said probe comprising a temperature sensing electrical device; and an electrical resistance heating device contained within the probe, heating said probe to a predetermined temperature by means of said electrical resistance heating device; and immersing said probe in the said coolant sample and measuring the electrical response of said temperature sensing electrical device for a predetermined period of time, and comparing said electrical response to a response in a reference liquid to determine said quenchability.

According to another aspect of the invention, there is provided an apparatus for controlling cooling of an object by directing a coolant onto said article, comprising: a coolant directing flow device for receiving a flow of coolant and for directing said coolant into contact with said object; a system for measuring quenching properties of said coolant flowing to said directing device; and a control system controlling a property of said flow of coolant to said directing device in response to quenching properties of said coolant measured by said system to achieve a desired cooling effect; wherein said system for measuring said quenching properties comprises: a coolant sample container in fluid communication with the coolant flowing to said device, a probe for immersion into said coolant in said sample container, a temperature sensing electrical device forming part of said probe and generating electrical signals corresponding temperatures sensed, and electrical resistance heating device forming part of said probe, an immersion system for immersing the said probe into said coolant, and electrical circuitry for measuring quenchant properties of said coolant from said electrical signals and for directing said control system to control said property of said coolant to said device to achieve said desired cooling effect.

According to yet another aspect of the invention, there is provided a method of controlling the cooling of an object by a coolant, comprising the steps of: obtaining a substantially stagnant sample of said coolant; measuring quenchability of said coolant of said sample; and modifying a property of said coolant brought into contact with said object responsive to a measured quenchability of coolant of said stagnant sample to achieve a desired cooling effect; wherein said quenchability is measured by providing a probe for immersion in said liquid coolant, said probe having a temperature sensing electrical device forming part of said probe; heating said probe to a predetermined temperature at an average rate of at least 40° C./second; and immersing said probe in the said coolant sample and measuring the electrical response of said temperature sensing electrical device for a predetermined period of time, and comparing said electrical response to a response in a reference liquid to determine said quenchability.

The temperature sensing electrical device and the electrical resistance heating device contained within or part of the probe for immersion in the coolant are preferably electrically connected to each other, preferably within the probe.

The coolant sample container may preferably in use be isolated by means of valves or other arrangements so that the sample can be kept substantially stagnant during the period in which the probe is immersed in the sample.

The probe is preferably heated at an average rate of at least 40° C./second by any means capable of heating the probe in a gas, such as air, at that rate. Induction heaters may be used, but a direct electrical resistance heating circuit which is in electrical connection with the temperature sensing electrical device is preferred. It is further preferred that the probe be heated at an average rate of at least 80° C./second.

The quenchability of the coolant is a measure of the rate of heat extraction by a particular coolant and can be quantified in a number of ways. It is preferably determined as the ratio of a representative time average of the temperature decay curve for the coolant for a pre-determined time period over the representative time average taken for a reference coolant at a reference temperature.

The preferred reference coolant is deionized distilled water at 20° C., but may be any other liquid.

The quenchability of the coolant is preferably determined as a "quenchability index" represented by the symbol "I" (see, for example, J. Langlais et al, "Measuring the heat extraction capacity of DC casting cooling water" in Light Metals 1995, Page 979) described by the following equation:

$$I = \frac{S \times 100}{S_{DDW}^{20}}$$

where
I is the "quenchability index";
S is the average cooling rate of the probe for the coolant sample; and
$S_{DDW}^{20}$ is the average cooling rate of the probe for distilled/deionized water at 20° C.

The average cooling rate (of the coolant or the reference) is determined, for example, by $$S = \frac{\int dT/dt\, dt}{\Delta t}$$

where the integration is taken over a predetermined time period.

The average cooling rate could also be taken as the temperature gradient at some predetermined time (being the same for both coolant and the reference).

The quenchability index therefore has a value of 100 for distilled/deionized water at 20° C.

The representative time average of the temperature decay may also be based on the time integral of the temperature decay curve itself, taken over the same predetermined time period for both coolant and reference. The use of the average of the temperature gradient has a theoretical significance in that the average heat extraction rate from the probe is proportional to this quantity.

The cooling rates are generally obtained by monitoring the temperature decay of the probe following immersion in a coolant, and calculating the average rate of change of temperature over a predetermined time period.

Other versions of the index may use the ratio of the integrated temperature decay curve over equal and predetermined time periods as well.

The temperature sensing electrical device may be, for example, an electrical resistance thermometer, a thermistor or a thermocouple junction. In practice, the temperature sensing electrical device is most preferably a thermocouple junction. In this case, the electrical resistance heating circuit is preferably connected to the thermocouple junction by means of wires that have the same composition as one of the wires in the thermocouple junction.

The temperature sensing electrical device as well as being electrically connected to the electrical resistance heating device is preferably part of the electrical resistance heating circuit. In the case of an electrical resistance thermometer or thermistor, the resistance of the device itself will contribute to probe heating when a current is applied. In the case of a thermocouple junction, the junction may have sufficient resistance to contribute to heating, when a current is applied through the pair of electrical resistance heating wires, or may represent an electrical connection between the pair or heating wires.

It is preferred that the heating wires and thermocouple wires be made from alloys that are resistant to oxidation at temperatures of up to 600° C.

The thermocouple junction is preferably a Pt-Pt/10% Rh junction and the connecting wires to the electrical resistance heating circuit are preferably Pt/Rh since these provide a higher resistance than Pt in the heating circuit.

The immersion probe may be formed from one of the metals of the thermocouple junction and is electrically connected to the junction. It may also be formed by fusing together the four wires (for example 1 Pt and 3 Pt/Rh) and shaping the result to the desired form. Although the resulting composition of the fused junction differs slightly from the wire composition, no additional electromotive force (emf) signal develops because of the small size of the contact.

The probe is normally made as small as possible to achieve the desired fast measurement time and preferably has a mass and heat capacity that is capable of being heated (in air) at an average rate of at least 40° C./second, more preferably at an average rate of at least 80° C./second, between ambient temperature and a predetermined higher temperature. The predetermined higher temperature is preferably above the film boiling temperature of the coolant, more preferably above 400° C., and most preferably above the surface temperature of the body to be cooled by the coolant.

The probe may be immersed in the coolant by lowering it into a sample of the coolant, or by changing the level of coolant within a container surrounding the probe. The coolant level may be changed by alternately pumping coolant into the surrounding container and draining or pumping the coolant out of this container, or by using a container that forms an airtight seal in cooperation with the coolant, and applying and releasing a vacuum to raise the coolant level to contact the probe. The container with an airtight seal may also be operated by pressurizing the container to lower the coolant level below the level necessary to make contact with the probe, then releasing the pressure to allow the coolant to rise up and cover the probe. Of these various methods, it is particularly preferred to immerse the probe in the coolant by lowering it into a substantially stagnant sample of the coolant.

The coolant sample container is preferably in fluid communication with the coolant flow system used to cool the body to be cooled, and may have coolant supplied to it by means of a pump which causes a slow flow through the container, or via a filling valve which periodically fills and empties the container. The coolant in the sample container should be as quiescent or stagnant as possible during the measurement cycle to ensure maximum reproducibility of the measurements.

The coolant flow system is more preferably a coolant flow system used for cooling a solidified metal strand from a continuous or semi-continuous metal casting operation, and in particular is a coolant flow system used for DC casting of aluminum alloys. The measured quenchability parameter is used within a control system and compared to a predetermined target value for the property. Based on the difference between the two a property of the coolant used to cool the strand is modified in one or more ways. The property modified may include the flow of coolant, the pulsation rate (when the coolant is applied as a pulsating flow), the impingement angle of the secondary coolant, the gas content of the coolant, or the specific content of chemical additives used to alter the coolant chemistry (for example by changing the amount of residual oil in the coolant in a recycle type coolant system).

The preferred property to modify is the flow rate of the coolant. This may be varied in response to the deviations of the measured quenchability parameter from the predetermined target. The present quenchability measurement method provides a rapidly updated measurement of the parameter, but the time response of the measurement is most suited for controlling water flow rather than a control device capable of or requiring faster time responses.

The method of control may be used when appropriate during the course of a DC casting operation itself (for example, control of water flow) or, where a slower response is intrinsic to the system, between casting runs (for example, control of coolant chemistry).

The probe device of the present invention is capable of completing a heat-up and quench measurement in less than 20 seconds, and more typically in less than 10 seconds, permitting rapid repetition rates to be achieved and making possible the use of the device in control applications.

DETAILED DESCRIPTION OF THE PREFERRED EMBODIMENTS

Figure 1:
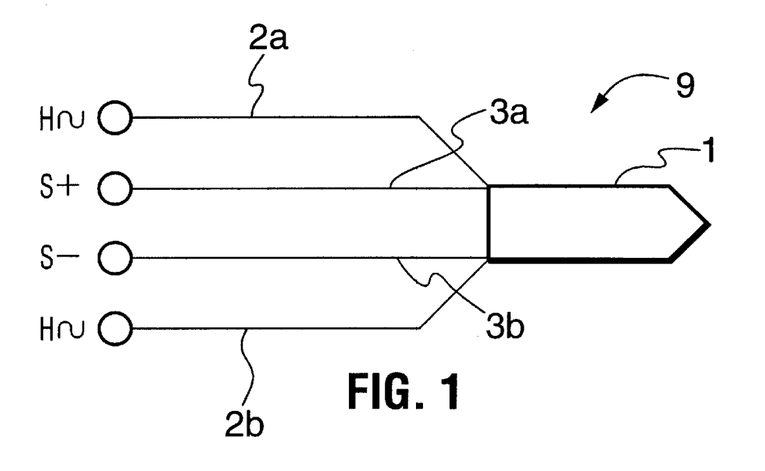
FIG. 1 shows a probe and electrical connections used in one preferred embodiment of this invention, the symbol H indicating heating heads and the symbol S indicating signal leads.

FIG. 1 shows one form of a thermocouple probe 9 suitable for use in the present invention. The probe consists of a small block 1 of Pt/10% Rh alloy having a square cross-section 6f about 1 mm×1 mm and about 5 mm in length. One end of the block is formed into a point, as shown. The block has a total weight of about 1 gram. Two heating leads 2a, 2b formed from the same Pt-10% Rh alloy as the small block are attached to the block. Two signal leads 3a, 3b, are also attached to the block. One signal lead is formed from Pt-10% Rh alloy and the other signal lead is formed from Pt. All of the leads may be attached to the block or welded together to form the block 1. The shape of the tip is not critical, but the tip should have as low a thermal mass as possible. As indicated, the preferred materials are Pt and Pt/10% Rh, but any other combination of alloys that give stable and readable thermal emf signals may be used. For example, copper-constantan combinations or chromel-alumel combinations may be used. However, the heating wires and one of the signal wires, plus the tip, are preferably manufactured from one of the materials, and the second signal wire from the other.

Figure 2:
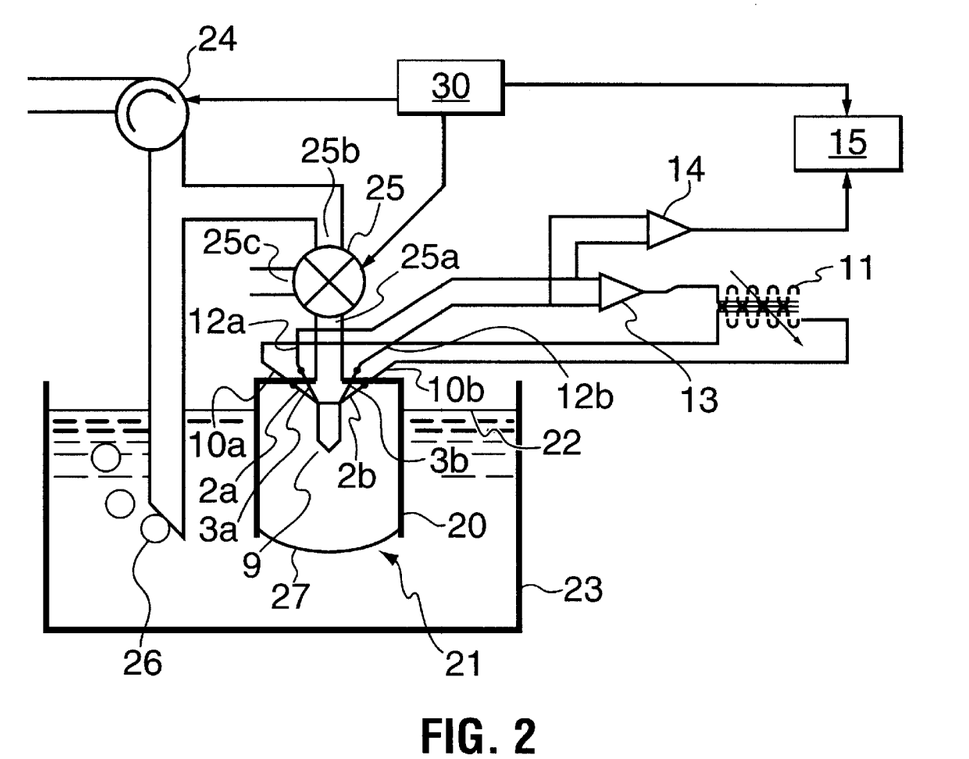
FIG. 2 shows the probe, electrical circuits and method of immersion used in one embodiment of this invention.

FIG. 2 shows a probe temperature control and monitoring system suitable for use with the probe of FIG. 1, and one embodiment of a system suitable for immersing the probe in a coolant.

Heating connections 2a, 2b of the probe 9 are connected via wires 10a, 10b to an output of a variable AC power supply 11—for example, a toroidal transformer (e.g. 40v, 225 VA output). This in turn is controlled by a feedback controller 13 which responds to the thermal emf measured by leads 12a, 12b connected to the signal leads 3a, 3b. A second differentiating circuit 14 provides a signal proportional to the time derivative of the measured temperature which is recorder at recorder 15 and displayed. The derivative signal is used to obtain the quenching index. The leads 12a, 12b are manufactured from the same alloy as leads 3a, 3b, respectively, and lead 12a is joined to 3a, and the lead 12b is joined to 3b, preferably by fusing the materials together. The leads 10a, 10b may be manufactured from any suitable metal (for example copper) and are joined to leads 2a, 2b by brazing (e.g. silver soldering).

The immersion of the probe is controlled by use of a pressurized container surrounding the probe. For this purpose, an airtight container 20 is provided in the form of an inverted cup, with the open end 21 immersed below the level of coolant 22 held within a sample container 23. The container 20 is initially pressurized using a pump 24 and a two-position valve 25 where pressurization is accomplished by having ports 25a and 25b connected.

The maximum pressure that can be applied is established by use of a bubbler 26 which relieves any excess pressure beyond that which is necessary to force the coolant level to a position shown by the meniscus 27. There is no gas flow through the airtight container in this mode of operation.

When the ports 25a and 25c of the two-position valve are interconnected, the pressure in the airtight container is rapidly released and the coolant level rises to approximately the same level as in the sample container 23, thus immersing the probe 9 in coolant.

A process controller 30 is used to control the sequence of operations as follows:

Upon starting the measurement sequence, the valve 25 is operated to lower the coolant level to the bottom of the pressurized container 20. The temperature recording is turned off. A heating current is applied to the heating wires 2a, 2b and the device is heated to a predetermined temperature (e.g. over 400° C.) and held for a few seconds to stabilize the temperature. The heater circuit is then deactivated and the temperature recorder is started and the temperature is monitored for a few seconds until it falls to a predetermined level about 50° C. less than the previous temperature, at which time valve 25 is activated to cause the coolant level to rise rapidly and immerse the probe. The temperature and differential temperature are continuously monitored until the temperature falls below the level of interest. The initial steps of the measurement up to the point of immersion take only 30 seconds or less.

Figure 3:
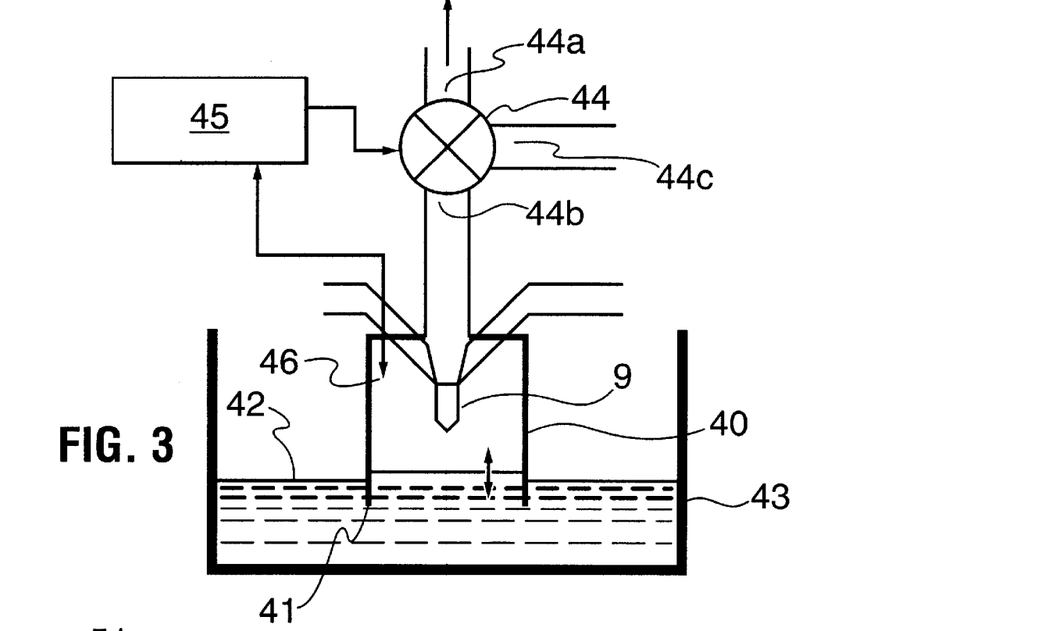
FIG. 3 shows the probe, the probe electrical connections and method of immersion used in another embodiment of this invention.

FIG. 3 shows a second method for controlling the immersion of the probe 9. Only the probe and connecting wires are shown in FIG. 3. The probe is contained within an airtight container in the form of an inverted cup 40, sealed at its lower end 41 by immersion below the coolant level 42 in a sample container 43. A two-way valve 44 is provided connected to the airtight container, with one port 44a connected to a vacuum system (not shown), and a port 44b connected to the airtight container. A third port 44c is open to the atmosphere. In use, when the probe is to be immersed, the controller 45 activates the valve 44 so that ports 44a and 44b are connected in order to allow the vacuum system to draw the coolant up into the airtight container. A level sensor 46 is provided which disconnects the two ports when the coolant reaches a level that covers the probe 9. Once the measurement is completed, the ports 44c, 44b are connected and the coolant level falls to its initial level.

Figure 4:
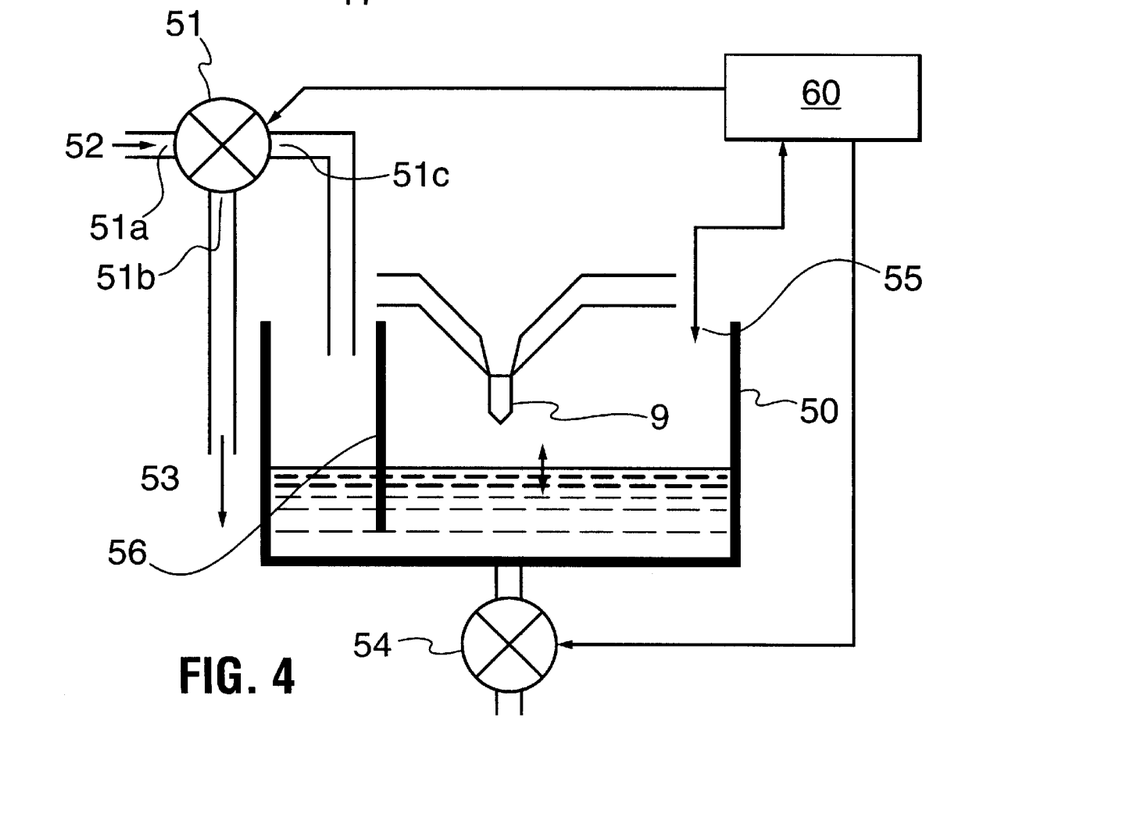
FIG. 4 shows the probe, the probe electrical connections and method of immersion used in yet another embodiment of this invention.

FIG. 4 shows a third method for controlling immersion of the probe. Only the probe and connecting wires are shown in FIG. 4. The coolant is contained in a sample container 50. A two-way coolant control valve 51 is provided. In "standby" operation, ports 51a and 51b are interconnected and coolant entering at 52 by-passes the measurement system, exiting at 53. A drainage valve 54 in the bottom of the sample container is provided and is "open" at this stage, substantially emptying the container of coolant. The coolant may also be removed by a pumpout system (not shown). In use, the controller 60 closes valve 54 and causes ports 51a and 51c to be interconnected, filling the container with coolant. A level detector 55 causes the controller to switch the valve 51 to its standby position when the coolant immerses the probe 9. When the measurement is complete, valve 54 again opens to drain the coolant. A baffle plate 56, having an opening at the bottom and fixed, for example, to the sides of the sample container, is preferably included to reduce the turbulence caused by the addition of coolant in this embodiment and thus produce a more stagnant or quiescent sample for analysis.

Figure 5:
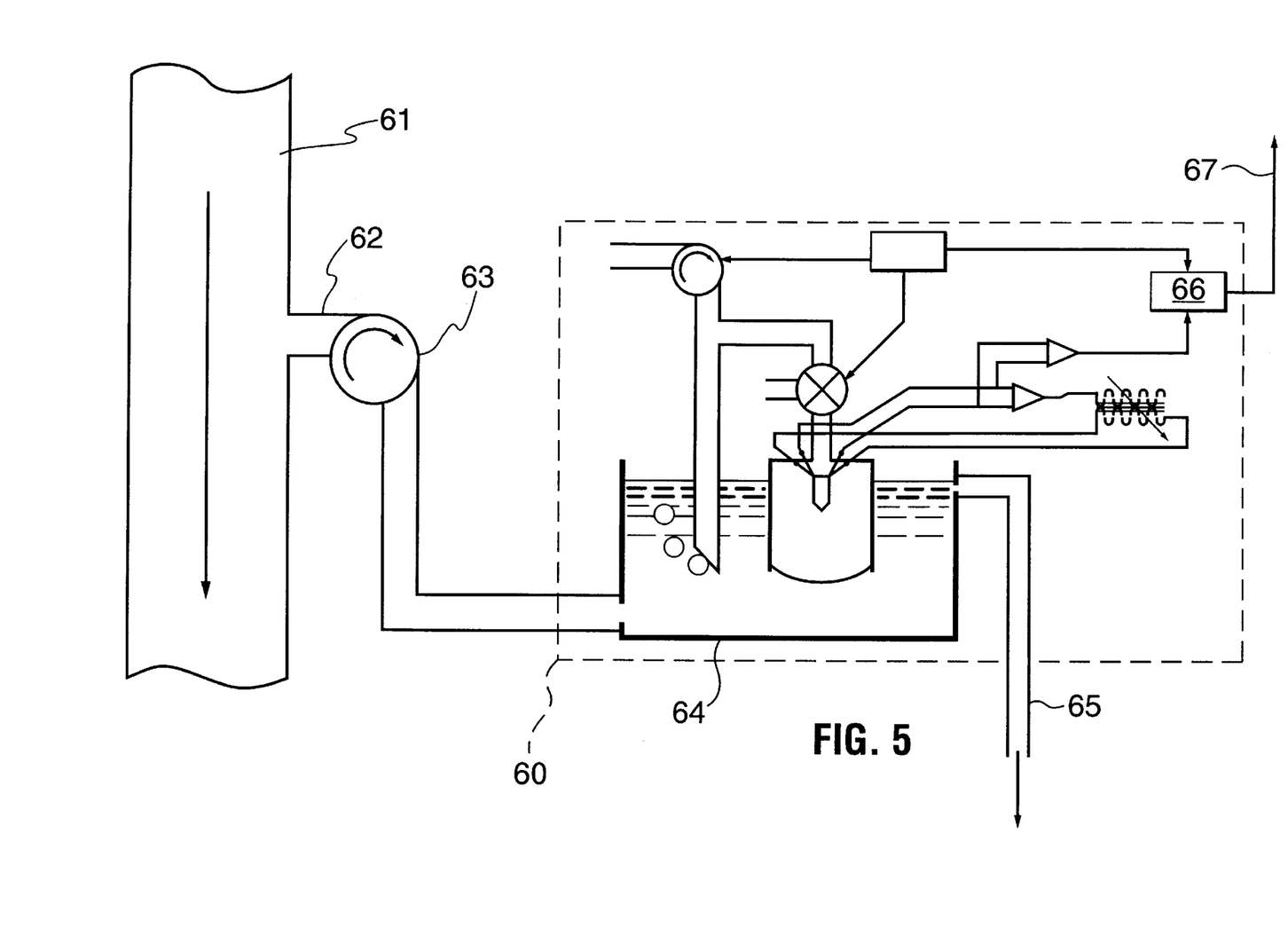
FIG. 5 shown the probe, electrical circuits and method of immersion as in FIG. 2 used as part of an in-line coolant control system.

FIG. 5 shows how the measurement and immersion control system of FIG. 2 is used in a control system for a DC casting coolant system. The measurement and control system of FIG. 2 is shown on a reduced scale within imaginary box 60. The DC casting coolant flows though pipe 61, for example, between a coolant storage reservoir and a DC casting mould table (neither of which shown in this Figure). A side arm 62 is provided on the coolant pipe as well as a pump 63 which causes a small portion of the coolant to flow through the sample container 64. The outlet of the sample container is set at a level that controls the coolant level as required for operation of the immersion control system as described above. The pump may not be required to maintain flow if suitable pipe sizes and coolant heads are chosen. The recording device 66 of the measurement system previously described is provided with a control output 67. The control output can be used to control various aspects of the casting process in response to the measured quench parameter. For example, the coolant flow rate may be altered to compensate for changes to coolant quench parameters, or the amount of coolant dumped and made up may be altered. Generally, some form of signal conditioning will be applied to the control output 67 to compensate for the periodic and intermittent nature of the measurement and the response time of the sampling system. The control output may also be stored and used on an intermittent basis (for example, between casts in a DC casting system) to reset the casting cooling parameters in a stepwise rather than semi-continuous fashion.

Figure 6:
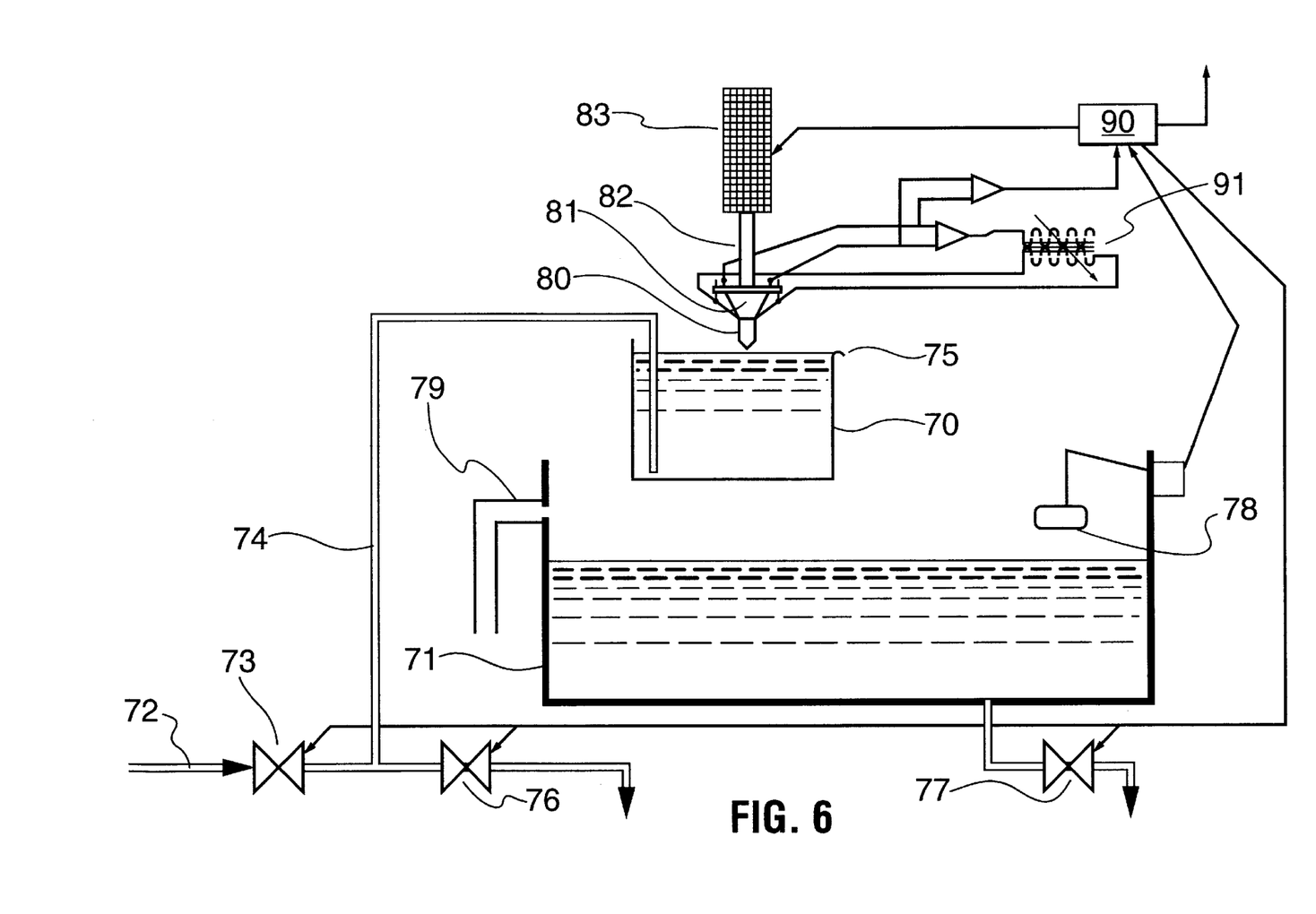
FIG. 6 shows the probe, electrical circuits and method of immersion as part of an in-line coolant control and monitoring system in yet another embodiment of the invention.

A further embodiment of the invention is shown in FIG. 6. A double container is used in this embodiment, with an inner container 70 located inside an outer container 71. The inner container is fed from an external coolant source 72 by means of a solenoid valve 73 and a feed pipe 74 which terminates inside and near the bottom of the inner container. The inner container also has an overflow lip 75 along a portion of its circumference, and the inner container is positioned such that any liquid overflowing the inner container via the overflow lip will collect in the outer container 71. A solenoid controlled syphon valve 76 is attached to the feed line 74, at a position well below the bottom of the inner vessel. The outer container is equipped with a solenoid drain valve 77, and float actuated switch 78, which is activated when liquid in the outer container reaches a predetermined level, and an overflow 79.

The probe 80 is a four wire probe of the type previously described. The four wires are firmly mounted in a ceramic (zirconia) block 81 which is cemented to a vertically oriented rod 82 which is in turn attached to the moving shaft of a solenoid 83.

The solenoid can be positioned in the vertical direction by a micrometer screw adjuster (not shown) and the travel of the solenoid shaft can also be adjusted. The inactive position of the solenoid is with the shaft and attached probe at the lowest position. In this position, the probe is positioned so that with the inner container filled to the point of overflow, the probe is immersed. In the activated position, the probe and shaft are in the highest position and the position is adjusted so that the probe tip is just clear of the surface coolant.

The valves 73 and 76 are normally closed and valve 77 is normally opened in the unactivated state.

A controller 90 is provided to control the sequence of measurements. The solenoid 83 is activated to raise the probe clear of any coolant in the inner container 70. Valve 73 is opened and valve 77 is closed. Coolant flows through tube 74 and fills the inner container. The valve remains open and coolant is allowed to overflow into the outer container 71, until it reaches a predetermined level that activates the float switch 78. The predetermined level is selected so that several complete changes (typically 10) of coolant flow through the inner container and ensure it is completely flushed from previous samples. The float switch is sensed by the controller which in turn closed valve 73 and opens valve 77 to drain the outer container and allow the coolant in the inner container to become stagnant.

The controller then activates the heater control 91 to cause the probe 80 to be heated to a predetermined temperature as described previously. At this stage the heater is switched off, the probe allowed to start to cool, and the solenoid is de-activated which rapidly immerses the probe to the pre-determined immersion in the coolant. Because only the minimum amount of probe travel necessary for it to function is used, and because the probe is preferentially pointed, the immersion causes little disturbance to the coolant. The temperature decay is recorded as previously described, and the quenchability index determined and displayed or used for control purposes as previously described. On completion of the measurement, valve 73 is briefly opened to refill the tube 74 with coolant that may have leaked out, then valve 73 is closed and siphon valve 76 is opened to cause most of the coolant in the inner container to be siphoned out to an external drain. Valve 76 is then closed to complete the measurement sequence.

Because the temperature decay is measured when all solenoids are in their unactivated states, and when the heater has been deactivated, noise from these sources is eliminated from the measurement.

Use of an essentially stagnant coolant sample and minimizing any disturbances to the coolant during the immersion step ensure that the temperature decay is measured under conditions where the effect of coolant movement on heat transfer and hence probe temperature changes is minimized.

These considerations ensure that highly reproducible measurements are possible, which become important in using the measurements to control coolant properties and flow.

In any of the above embodiments, measurements of "quenchability" are based on a relative index. This relative index is established as follows. A measurement is made in which distilled, deionized water at a pre-determined temperature (generally 20° C.) is substituted for the coolant. Using the same probe pre-heat temperature, and carrying out measurements in an identical manner, measurements are carried out on the actual coolant. The temperature decay, and in particular the average value of the time differential of temperatures, are determined for the same time periods and the ratio of the two is used as the "quenchability index."

The present apparatus permits periodic, but rapid, measurement of the quenchability index which therefore can be used in a control function.

Figure 7:
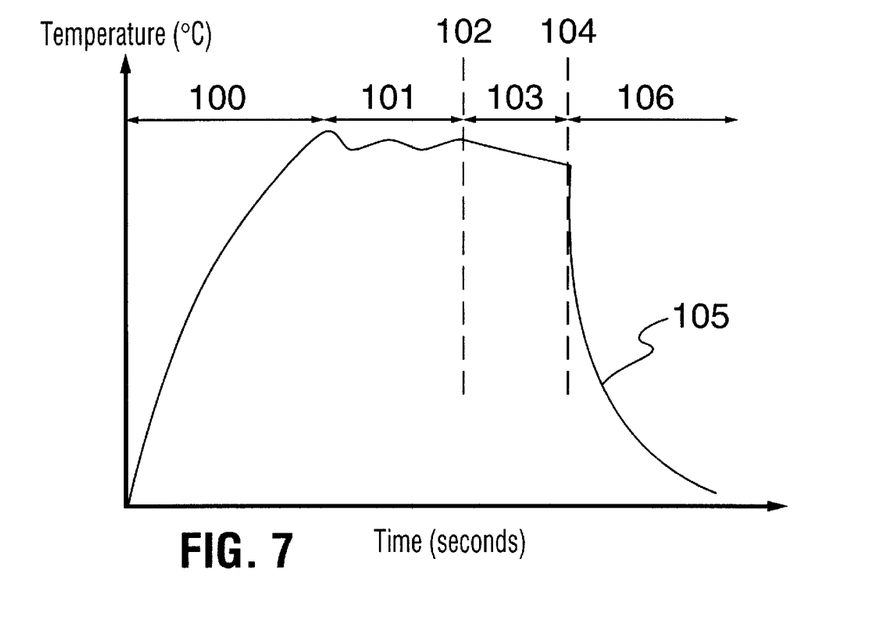
FIG. 7 shows a typical probe temperature profile as exhibited by the apparatus and method of this invention.

A typical probe temperature profile is shown in FIG. 7 which is a plot of the probe temperature (as measured by the connections to leads 3a, 3b) as a function of the time following the application of heater power to leads 2a, 2b. The probe temperature rises to a preset value (between about 400° C. and 600° C.) during a period 100 of less than about 5 seconds (typically 2 to 3 seconds). It is held at this target temperature (using the measured temperature to control the heater power circuit) for a period 101 of less than about 2 seconds, at which time 102 the heater circuit is deactivated. The temperature of the probe (still not immersed in the coolant) is allowed to fall naturally for a period 103 of about 1 second, for a total elapsed time of less than about 8 seconds, at which time 104 the probe is rapidly immersed in the coolant. The temperature decay profile 105 (and the differential of this profile) is measured during a period 106 of less than about 4 seconds, which is well in excess of the time (0.2 to 0.3 seconds) over which temperature measurement is required to define the decay curve.

Figure 8:
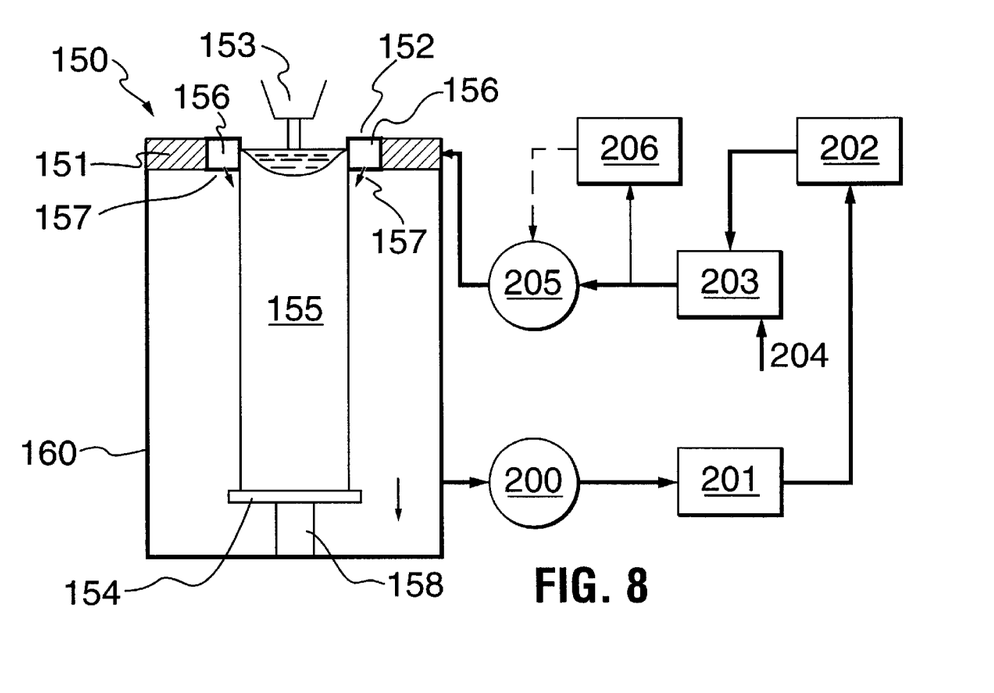
FIG. 8 shows a typical implementation of the present invention to control coolant flow during a casting operation.

The quenchability measurement device of the present invention is shown as part of a coolant flow control system in FIG. 8. This Figure shows a typical DC ingot casting machine 150 and associated coolant system. The ingot casting machine includes a casting table 151 in which are mounted one or more open ended casting moulds 152. The casting moulds are fed by a metal feed system 153 (which generally also includes a metal flow control system designed to maintain the molten metal at a predetermined level within the mould during casting). A base or stool cap 154 initially closes the bottom of the casting mould, and as casting proceeds is lowered to permit the cast ingot 155 to descend from the mould. The casting mould is most frequently designed to contain internal water channels 156 to provide primary cooling of the ingot (to form an initial shell of solidified metal) and openings 157 from which coolant directly sprays onto the ingot surface just below the mould to provide secondary cooling. The secondary cooling openings are generally fed from the primary cooling channels. Coolant is therefore fed from the coolant control system to the primary cooling channels and then discharges as the secondary coolant. The casting table base and base lowering mechanism 158 is mounted in the top of a casting pit 160. Secondary coolant is collected in the bottom of the casting pit.

The coolant control system shown in FIG. 8 is of a closed loop type. Coolant which has collected in the bottom of the casting pit is pumped by a pump 200 into a coolant purification system 201. This system removes excess oil and other contaminants by a variety of treatment techniques such as flotation, filtration, etc. The cleaned coolant then passes through a heat exchanger 202 or cooling tower to remove excess heat. A surge tank 203 is generally also included. Make up water 204 or other chemicals (biocides, corrosion inhibitors, etc, can also be added here or elsewhere in the system). The coolant is then pumped back to the casting machine (primary coolant channels) via a pump 205. According to the present invention, a quenchability measurement circuit 206 of the type already described (and as illustrated in FIG. 5 and 6 for example) is connected to the coolant feedpipe leaving the surge tank. The quenchability index measured by the circuit generated a control output as described which is fed to the speed control of pump 205 to adjust the water flow rate. In practice, for example, if the quenchability index falls below a desired predetermined value, the water flow will be increased to compensate for the reduced heat removal capability of the coolant.

What we claim is:

1. A method of measuring quenchability of a liquid coolant, comprising the steps of:

obtaining a substantially stagnant simple of said liquid coolant;

providing a probe for immersion in said sample, said probe containing a temperature-sensing electrical device which generates an electrical response corresponding to temperature sensed;

said probe forming part of an electrical circuit provided for heating the probe, and functioning at least in part as an electrical heating device when said circuit is energized;

by means of said electrical resistance heating circuit, heating said probe in a gas to a predetermined temperature measured by the electrical response of said temperature sensing device;

immersing the said probe into said sample and measuring the electrical response for a predetermined measurement period, and comparing the measured electrical response to a response of a reference liquid measured under equivalent conditions; and determining quenchability of the liquid coolant from said responses.

2. The method of claim 1, wherein the quenchability of the coolant is determined as a ratio of a representative time average of a temperature decay curve for the coolant for a predetermined time period, relative to a representative time average taken for a reference coolant at a reference temperature.

3. The method of claim 1, wherein said sample is held static when said electrical probe is immersed therein and for said predetermined measurement period.

4. The method of claim 1, wherein said probe is held static while said probe is immersed into said sample.

5. The method of claim 1, wherein said response of a reference liquid is a response of deionized distilled water held at 20° C.

6. The method of claim 1, wherein said probe is heated by said circuit at an average rate of at least 40° C./sec.

7. The method of claim 1, wherein said probe is heated by said circuit at an average rate of at least 80° C./sec.

8. The method of claim 1, wherein said probe is heated by said circuit to a temperature of at least 400° C.

9. A method of claim 1 wherein the said temperature sensing electrical device and the said electrical resistance heating device are electrically connected within the said probe.

10. A method of claim 1 wherein said temperature-sensing electrical device also forms part of said electrical circuit.

11. A method of measuring the quenchability of a liquid coolant, involving obtaining a substantially stagnant sample of the liquid coolant, providing a probe for immersion in the sample, the probe containing a temperature-sensing electrical device which generates an electrical response corresponding to a temperature sensed, heating the probe in a gas, at an average rate that exceeds 40° C./second, to a predetermined temperature measured by the electrical response of the temperature sensing device, immersing the probe into the sample and measuring the electrical response for a predetermined measurement period, and comparing the measured electrical response to a response of a reference liquid measured under equivalent conditions, to thereby determine the quenchability property of the liquid coolant.

12. An apparatus for measuring quenchability of a liquid coolant, comprising:

a probe for immersion in a sample of said liquid coolant, said probe forming a part of an electrical circuit provided for heating the probe, and functioning at least in part as an electrical heating device when said circuit is energized; and a temperature sensing electrical device contained within said probe.

13. Apparatus according to claim 12, wherein wherein said temperature-sensing electrical device also forms part of said electrical circuit.

14. The apparatus of claim 12, wherein the said temperature sensing electrical device and the said electrical resistance heating circuit are electrically connected.

15. The apparatus of claim 12, wherein said probe comprises a block of metal alloy tapering to a point at an end that is first immersed into said sample of coolant.

16. The apparatus of claim 15, wherein said alloy is a platinum/rhodium alloy.

17. The apparatus of claim 12, wherein said temperature sensing device is selected from the group consisting of an electrical resistance thermometer, a thermistor and a thermocouple junction.

18. The apparatus of claim 12, wherein said temperature sensing device is a thermocouple junction.

19. The apparatus of claim 18, wherein the thermocouple junction is a Pt-Pt/10% Rh junction.

20. The apparatus of claim 18, wherein said probe is formed by fusing together four wires forming the thermocouple junction and said heating circuit.

21. The apparatus of claim 12, having a thermal mass such that said probe is heated at an average rate of at least 40° C./sec by said circuit.

22. The apparatus of claim 12, having a thermal mass such that said probe is heated at an average rate of at least 80° C./sec by said circuit.

23. The apparatus of claim 12, wherein said probe has dimensions no larger than about 1 mm×1 mm×5 mm.

24. The apparatus of claim 12, comprising electrical connections for electrical signals generated by said temperature sensing electrical device, and electrical connections for said heating circuit.

25. A method of controlling the cooling of an object by contacting the said object with a coolant, comprising the steps of:

obtaining a substantially stagnant sample of said coolant;

measuring quenchability of said coolant of said sample; and controlling a property of said coolant coming into contact with said object responsive to a measured quenchability of said coolant of said stagnant sample to achieve a desired cooling effect;

wherein said quenchability is measured by providing a probe for immersion in said liquid coolant, said probe comprising a temperature sensing electrical device; and an electrical resistance heating device contained within the probe, heating said probe to a predetermined temperature by means of said electrical resistance heating device; and immersing said probe in the said coolant sample and measuring the electrical response of said temperature sensing electrical device for a predetermined period of time, and comparing said electrical response to a response in a reference liquid to determine said quenchability.

26. A method of claim 25 wherein the said temperature sensing electrical device and the said electrical resistance heating device are electrically connected within the said probe.

27. A method of claim 25 wherein said property is the flow rate of said coolant.

28. An apparatus for controlling cooling of an object by directing a coolant onto said article, comprising:
- a coolant directing flow device for receiving a flow of coolant and for directing said coolant into contact with said object;
- a system for measuring quenching properties of said coolant flowing to said directing device; and
- a control system controlling a property of said flow of coolant to said directing device in response to quenching properties of said coolant measured by said system to achieve a desired cooling effect;

wherein said system for measuring said quenching properties comprises:
- a coolant sample container in fluid communication with the coolant flowing to said device,
- a probe for immersion into said coolant in said sample container,
- a temperature sensing electrical device forming part of said probe and generating electrical signals corresponding temperatures sensed, and electrical resistance heating device forming part of said probe,
- an immersion system for immersing the said probe into said coolant, and
- electrical circuitry for measuring quenchant properties of said coolant from said electrical signals and for directing said control system to control said property of said coolant to said device to achieve said desired cooling effect.

29. An apparatus of claim 28 wherein the said temperature sensing electrical device and said electrical resistance heating device are electrically connected within the said probe.

30. The apparatus of claim 28, wherein said immersion system is selected from the group consisting of a lowering mechanism for lowering the probe into said coolant, and a liquid pump for raising a level of said coolant in said sample container.

31. The apparatus of claim 28, wherein said coolant control system is selected from the group consisting of a coolant flow control system, a coolant pulsation control system, and a coolant additive control system.

32. The apparatus of claim 28, wherein said temperature sensing electrical device is a thermocouple junction formed by two wires of different composition, and wherein the electrical resistance heating circuit is connected to the thermocouple junction by means of wires that have the same composition as one of the wires of the thermocouple junction.

33. The apparatus of claim 32, wherein the heating wires and thermocouple wires be made from alloys that are resistant to oxidation at temperatures of up to 600° C.

34. The apparatus of claim 32, wherein the thermocouple junction is a Pt-Pt/10% Rh junction and the connecting wires to the electrical resistance heating circuit are Pt/Rh.

35. A method of controlling the cooling of an object by a coolant, comprising the steps of: obtaining a substantially stagnant sample of said coolant; measuring quenchability of said coolant of said sample; and modifying a property of said coolant brought into contact with said object responsive to a measured quenchability of coolant of said stagnant sample to achieve a desired cooling effect; wherein said quenchability is measured by providing a probe for immersion in said liquid coolant, said probe having a temperature sensing electrical device forming part of said probe; heating said probe to a predetermined temperature at an average rate of at least 40° C./second; and immersing said probe in the said coolant sample and measuring the electrical response of said temperature sensing electrical device for a predetermined period of time, and comparing said electrical response to a response in a reference liquid to determine said quenchability.

* * * * *